United States Patent [19]

Tanaka et al.

[11] Patent Number: 4,718,425
[45] Date of Patent: Jan. 12, 1988

[54] CATHETER WITH PRESSURE SENSOR

[75] Inventors: Junsuke Tanaka; Ikuo Inage; Teruo Hyugaji, all of Yokohama, Japan

[73] Assignee: Mitsui Toatsu Chemicals Incorporated, Tokyo, Japan

[21] Appl. No.: 866,668

[22] Filed: May 27, 1986

[30] Foreign Application Priority Data

May 29, 1985 [JP] Japan .................. 60-114262

[51] Int. Cl.⁴ ............................................. A61B 5/02
[52] U.S. Cl. ................................. 128/673; 128/772; 604/280
[58] Field of Search ................. 128/672–673, 128/675, 748, 772, 642, 656–658, 715, 786; 604/280–281

[56] References Cited

U.S. PATENT DOCUMENTS

| 2,211,975 | 8/1940 | Hendrickson | 604/282 |
|---|---|---|---|
| 2,976,865 | 3/1961 | Shipley | 128/675 |
| 3,874,369 | 4/1975 | Pannier et al. | 128/674 |
| 4,073,287 | 2/1978 | Bradley et al. | 128/642 |
| 4,136,681 | 1/1979 | Hon | 604/171 X |
| 4,192,319 | 3/1980 | Hargens et al. | 128/673 X |
| 4,214,594 | 7/1980 | Little | 128/786 |
| 4,252,131 | 2/1981 | Hon et al. | 128/673 X |
| 4,281,660 | 8/1981 | Fujiwara | 128/642 |
| 4,304,240 | 12/1981 | Perlin | 128/786 X |
| 4,325,387 | 4/1982 | Helfer | 128/772 X |
| 4,369,790 | 1/1983 | McCarthy | 604/280 |
| 4,484,583 | 11/1984 | Graham | 128/715 X |
| 4,563,181 | 1/1986 | Wijayarathna et al. | 604/280 |
| 4,650,472 | 3/1987 | Bates | 128/658 X |

FOREIGN PATENT DOCUMENTS 863535 3/1961 United Kingdom .

Primary Examiner—Kyle L. Howell
Assistant Examiner—Angela D. Sykes
Attorney, Agent, or Firm—Millen & White

[57] ABSTRACT

A catheter equipped with a pressure sensor, which is composed of a fine insertion tube provided with the pressure sensor at the tip thereof and having sufficient stiffness to permit its insertion into and through a blood vessel and a fine and flexible guide tube connected to the fine insertion tube.

7 Claims, 4 Drawing Figures

CATHETER WITH PRESSURE SENSOR

BACKGROUND OF THE INVENTION

1. Field of the Invention

This invention relates to a catheter equipped with a pressure sensor and adapted to measure the blood pressure in the cardiovascular system, particularly, in the left ventricle of an animal to be tested. The term "animal" as used herein should be construed in a broad sense so that it embraces mammals, particularly, experimental mammals and patients.

2. Description of the Prior Art

It is often required to determine the waveforms of blood pressures of animals over long periods of time under non-anesthetic conditions, for example, in order to conduct efficacy tests on heart medicines or to effect diagnoses of circulatory organs.

For these purposes, catheters equipped with pressure sensors at the tips thereof are employed.

Conventional catheters of the above sort are however formed of woven "DACRON" ® or the like from the viewpoint of imparting hardness suitable for insertion into and through blood vessels. Accordingly, these conventional catheters frequently developed such problems that they were themselves bent by animals' movements and their internal lead wires were broken and disconnected.

SUMMARY OF THE INVENTION

An object of this invention is to provide a catheter which has a pressure sensor and permits its insertion into the circulatory organ system, especially, the left ventricle of an animal to be tested, so that it can be held there for a long period of time to permit continuous and smooth monitoring of the blood pressure.

As a result of various researches, the present inventors have achieved the above object by dividing a catheter into a fine insertion tube, which is required to have sufficient stiffness to permit the insertion of itself and a pressure sensor provided thereon into and through a blood vessel of an animal, and a fine guide tube capable of guiding a lead wire to the outside of the body of the animal without failure while conforming with movements of the animal, and making the latter tube with a specified material.

DETAILED DESCRIPTION OF THE INVENTION

Figure 1:
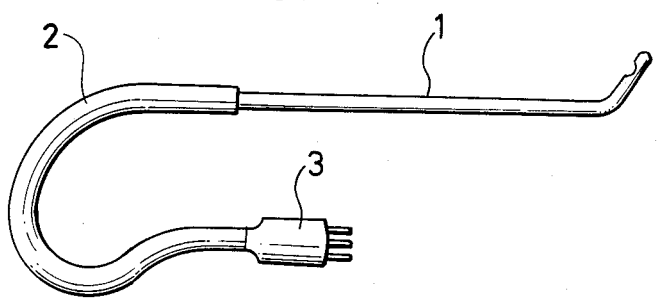
FIG. 1 is a perspective view of a catheter according to one embodiment of this invention.

In the catheter of this invention, the fine insertion tube required to have sufficient stiffness to permit its insertion into and through a blood vessel is also required to have both elasticity and hardness. Expressing the latter requirement in terms of tensile elasticity, it should preferably fall within a range of 25–150 kg. The value given above as tensile elasticity has been obtained in the following manner.

By using a tensile testing machine (for example, Instron type universal tester), a test tube is fixed with a chuck interval of 80 mm.

Increasing longitudinal stretching load (kg) is applied at a pulling rate of 1 mm/min to the test tube. In the course of the tensile test, elongations (mm) of the test tube are measured. These two values are plotted on an orthogonal coordinate system the origin of which corresponds to 0 (zero) load and 0 (zero) elongation.

Two fixed points are chosen on a straight line segment of the resulting graph. From the difference ($\Delta T$) between the stretching loads and the difference ($\Delta L$) between the elongations corresponding to these two points, the tensile elasticity of the test tube is determined as a solution for $$\frac{\Delta T \text{ (kg)}}{\Delta L \text{ (mm)}/80 \text{ (mm)}}.$$

The test is conducted at 23° C. and 60% (relative humidity).

The fine guide tube, through which its associated lead wire is smoothly guided to the outside of the body, is required to have sufficient flexibility so that it is not broken and can restore its original shape sufficiently even after bent with a small radius. Expressing this property in terms of tensile elasticity too, it may desirably be within a range of 1–10 kg.

As physical quantities indicative of flexibility, there are tensile elasticity, compressive elasticity, torsional elasticity, etc. They are mutually correlated. For fine tubes, their flexibility can be expressed in terms of tensile elasticity.

The above-described numeral ranges will next be described in further detail. The fine insertion tube of the above-described catheter is required to have a tensile elasticity of about 100 kg for its insertion into the left ventricle system and a tensile elasticity of about 50 kg for its insertion into the right ventricle. If a material having a tensile elasticity smaller than 25 kg is used, the resulting fine insertion tube per se is so soft that difficulties are encoutered in its insertion to a measurement site. On the other hand, any materials having tensile elasticity greater than 150 kg are too hard. There is thus a potential danger that the inner walls of blood vessels may be damaged. In addition, such hard catheters can hardly follow animals' movements, resulting in their damages at their entry sites in blood vessels.

In the present invention, the tensile elasticity of the fine guide tube of the catheter may preferably range from 1 kg to 10 kg. Any tensile elasticity smaller than 1 kg leads to difficulties in handling and is hence impractical. On the other hand, any tensile elasticity greater than 10 kg shows poor conformity to quick movements. A lead wire, which electrically connects a semiconductor pressure sensor to a connector provided outside the body, extends through the fine and flexible guide tube. Since the lead wire is also subjected to quick movements together with the fine guide tube in accordance with quick movements of the animal under a test, a usual enameled wire the strength of which is dependent primarily on the strength of a copper wire as its conductor does not have good durability against repeated bending and is often cut off during its application.

The lead wire is required to have durability against repeated bending. From this point of view, it is preferable to use a lead wire coated with TEFLON ® or the like to a thickness 0.5–1.5 times the diameter of the conductor. The strength of such a lead wire is primarily governed by the strength of its coating and the conductor is bent with greater radii, thereby showing good durability against repeated bending.

In view of conditions under which a catheter is used, the stiff part of the catheter is inserted into a blood vessel of an animal at a site, where the position of the blood vessel does not change significantly even if the animal moves a lot, and is held in place within the blood vessel. The catheter is therefore made of a hard but elastic material up to a lengthwise point where it is inserted in the blood vessel. On the other hand, the remaining part of the catheter, which extends out from the blood vessel to a point outside the body where the catheter is usually coupled to a connector, is preferably made of a flexible and highly-restorable material.

Incidentally, the actual lengthwise dimensions of these parts vary widely in accordance with the kind of each animal to be tested and the site of measurement and cannot be specified collectively.

The present invention will hereinafter be described in further detail with reference to the accompanying drawings, in which one embodiment of this invention is illustrated. It should however be borne in mind that the catheter shown in the drawings is merely illustrative of and the structure of the pressure-sensor equipped catheter of this invention is not necessarily limited to that shown in the drawings by way of example.

Referring first to FIG. 1, numeral 1 indicates a fine insertion tube which is a fine commercial tube forming a first portion of the catheter having a thickness of 7F (diameter: 2.3 mm) and length of 15 cm and made of woven "DACRON" ®. The length of 15 cm of the tube 1 is a length that is required for the tube 1 to reach at its tip portion the inside of the left ventricle of a dog when the tube 1 is inserted through a carotid artery of the dog. Designated at numeral 2 is a fine and flexible guide tube forming a second portion of the catheter having an outer diameter of 3.5 mm and length of 25 cm and made of soft polyvinyl chloride. The length of 25 cm of the tube 2 is a length that is required for the tube 2 to extend from the site of insertion into the blood vessel, under the skin of the dog, to a connector 3 provided on the back of the dog. The tensile elasticity of the fine guide tube 2 is 3.1 kg. The connector 3 is provided on the outer end of the tube 2.

Figure 2:
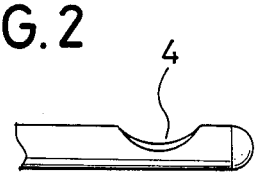
FIGS. 2 and 3 show, on an enlarged scale, a tip portion and joint portion of the catheter, respectively.

FIG. 2 illustrates, on an enlarged scale, a tip portion of the fine insertion tube 1 of FIG. 1. An elliptical recess 4 having a length of 3 m is formed at a location 5 mm apart from the tip. Inside the recess 4, there is provided a diaphragm semiconductor pressure sensor (not shown) which is sealed with silicone rubber. The semiconductor pressure sensor is electrically connected to the connector 3 by way of a lead wire (not shown) having a TEFLON ® coating of 0.08 mm thick and including a silver-plated copper wire of 0.08 mm in diameter as a conductor. The strength of the lead wire is dependent primarily on the TEFLON ® coating and the conductor is bent with greater radii. The lead wire is therefore durable against repeated bending and is not broken due to its bending by the animal's movements.

Figure 3:
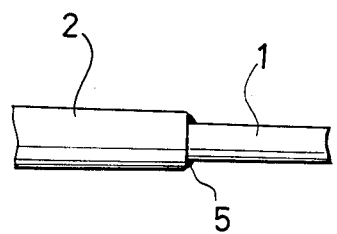

FIG. 3 shows, on an enlarged scale, a joint portion between the fine insertion tube 1 and fine guide tube 2. Since the hardness of the fine insertion tube 1 is different from that of the fine guide tube 2, they are prone to disconnection when moved. Thus, the fine guide tube 2 is connected to the fine insertion tube 1 with a rubber adhesive 5 of such properties that it adheres firmly to the fine inserted tube 1 and absorbs movements of the fine guide tube 2.

By using the catheter equipped with the pressure sensor and having the above-described structure, the blood pressure in the left ventricle of a dog was monitored under non-anesthetic conditions.

The fine insertion tube 1 was inserted through a carotid artery of the dog into its left ventricle. The fine guide tube 2 was allowed to extend from the entry site of the carotid artery, under the skin, to the back. The connector 3 was connected to an unillustrated FM transmitter (Model "ZB-671G"; manufactured by Nihon Kohden Corporation) which was carried on the back of the dog. Under the non-anesthetic conditions, the blood pressure in the left ventricle of the dog was monitored by means of a FM receiver unit (Model: "ZR-670G"; manufactured by Nihon Kohden Corporation). The catheter equipped with the pressure sensor did not develop any problems during for one month and allowed correct monitoring of the blood pressure in the left ventricle of the dog.

Figure 4:
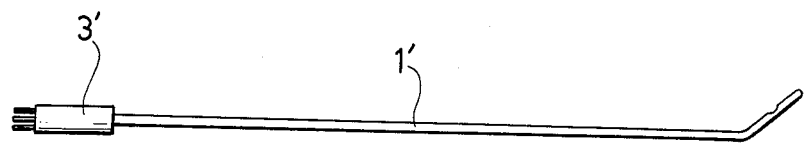
FIG. 4 is a perspective view of a conventional catheter equipped with a pressure sensor, which corresponds to the embodiment depicted in FIG. 1.

Referring next to FIG. 4 in which the conventional catheter equipped with the pressure sensor is depicted, a connector 3' is attached directly to a hard catheter 1' made of woven "DACRON" ®. An unillustrated enameled wire having a diameter of 0.1 mm is employed as a lead wire by which the pressure sensor and connector 3' are connected to each other. By using this conventional catheter equipped with the pressure sensor, the blood pressure in the left ventricle of a dog was monitored in the same manner. In only two days, the catheter was broken at the entry portion to the blood vessel and the lead wire was also disconnected by the dog's movements.

As has been described above, the pressure-sensor equipped catheter of this invention permits, owing to the use of the fine and flexible guide tube, precise and smooth monitoring of the waveform of the blood pressure of a non-anesthetized animal over a long period of time while holding it in the animal. When a catheter is inserted through a branched blood vessel, it is necessary to turn the catheter in various directions. Since a conventional pressure-sensor equipped catheter has a large torsional elasticity, its connector is also caused to turn in its entirety when the catheter is turned. It has thus been difficult to turn such a conventional pressure-sensor equipped catheter. On the other hand, the pressure-sensor equipped catheter of this invention makes use of the fine and flexible guide tube 2. Torsional forces are therefore absorbed by the fine and flexible guide tube 2 and the catheter can be turned without causing the connector 3 to turn. This facilitates the turning work of the catheter and hence the insertion of the catheter even in a branched blood vessel.

What is claimed is:

1. In a catheter for use in monitoring blood pressure in mammals, the catheter comprising a fine tube provided with (a) a pressure sensor at one end thereof, (b) an electrical connector at the opposite end and (c) a coated lead wire therein connected from the pressure sensor to the electrical connector; the improvement comprising: a fine tube having two portions, one portion being a fine insertion tube having a distal end with the pressure sensor located at the distal end thereof, the fine insertion tube having a tensile elasticity in the range of 25 to 150 Kg providing sufficient stiffness to permit its insertion into and along a blood vessel of the mammal to be monitored; the other portion of the fine tube being a flexible guide tube connected to the fine insertion tube at one end and having the connector at an opposite end, the guide tube having a length sufficient to reach the body surface of the mammal upon application of the catheter, thereby preventing breaking of the tube or disconnecting of the coated lead wire caused by the movement of the mammal.

2. A catheter as claimed in claim 1, wherein the fine insertion tube has a tensile elasticity of 25-150 kg.

3. A catheter as claimed in claim 1, wherein the fine guide tube has a tensile elasticity of 1-10 kg.

4. A catheter as claimed in claim 1, wherein the lead wire, which is adapted to guide signals from the pressure sensor to the outside of the body of the animal, has a coating of a thickness 0.5-1.5 times the diameter of a conductor of the lead wire.

5. In a catheter having a blood pressure sensor at one end thereof for use in monitoring blood pressure in active mammals by inserting a first portion of the catheter having the sensor thereon through a blood vessel of the mammal and having a second portion thereof extending beneath the skin of the mammal and emerging at a location exterior to the mammal for connection to a transmission means for conveying blood pressure information to a monitor; the improvement comprising:

the first portion being a tube made of woven DACRON, having a diameter sufficiently small to fit through a selected blood vessel of the mammal and a length sufficient to reach the left ventricle of the mammal from a point of insertion into the blood vessel, the first portion of the catheter having a tensile elasticity in the range of 25-150 kg;

the second portion of the catheter being a tube made of soft polyvinylchloride, having a diameter slightly greater than that of the first portion, having a tensile elasticity in the range of 1-10 kg and being bonded to the first portion by a rubber adhesive;

an electrical connector attached to the end of the second portion of the catheter for connection to the transmission means; and electrical lead means extending through the first and second portions of the catheter and being connected to the pressure sensor and the electrical connector, the electrical lead means having a TEFLON coating thereon in the range of 0.5 to 1.5 as thick as the diameter of the conductor means in the lead, whereby the catheter withstands flexing without breakage so that the blood pressure of the active mammal can be continuously monitored with minimal interference with the activities of the mammal.

6. The improvement of the claim 5 wherein the electrical lend means is silver-plated copper wire having a thickness of about 0.008 mm.

7. In a catheter for use in monitoring blood pressure in mammals, the catheter comprising a fine tube provided with (a) a pressure sensor at one end thereof, (b) an electrical connector at the opposite end and (c) a coated lead wire therein connected from the pressure sensor to the electrical connector; the improvement comprising: a fine tube having two portions, one portion being a fine insertion tube having a distal end with the pressure sensor located at the distal end thereof, the fine insertion tube having sufficient stiffness to permit its insertion into and along a blood vessel of the mammal to be monitored; the other portion of the fine tube being a flexible guide tube having a tensile elasticity in the range of 1-10 Kg connected to the fine insertion tube at one end and having the connector at an opposite end, the guide tube having a length sufficient to reach the body surface of the mammal upon application of the catheter, thereby preventing breaking of the tube or disconnecting of the coated lead wire caused by the movement of the mammal.

* * * * *